(12) United States Patent
Varghese et al.

(10) Patent No.: US 10,517,674 B2
(45) Date of Patent: Dec. 31, 2019

(54) DEVICE FOR NON-INVASIVE TREATMENT OF SKIN USING LASER LIGHT

(71) Applicant: KONINKLIJKE PHILIPS N.V., Eindhoven (NL)

(72) Inventors: Babu Varghese, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 720 days.

(21) Appl. No.: 14/778,130

(22) PCT Filed: Mar. 17, 2014

(86) PCT No.: PCT/IB2014/059880
§ 371 (c)(1),
(2) Date: Sep. 18, 2015

(87) PCT Pub. No.: WO2014/147543
PCT Pub. Date: Sep. 25, 2014

(65) Prior Publication Data
US 2016/0270848 A1    Sep. 22, 2016

Related U.S. Application Data

(60) Provisional application No. 61/804,254, filed on Mar. 22, 2013.

(51) Int. Cl.
*A61N 5/06* (2006.01)
*A61B 18/20* (2006.01)
(Continued)

(52) U.S. Cl.
CPC .. *A61B 18/203* (2013.01); *A61B 2017/00066* (2013.01); *A61B 2018/0047* (2013.01); *A61B 2018/00642* (2013.01)

(58) Field of Classification Search
CPC ........ A61B 18/203; A61B 2017/00066; A61B 2018/0047; A61B 2018/00642;
(Continued)

(56) References Cited

U.S. PATENT DOCUMENTS 4,592,361 A * 6/1986 Parker .................. A61B 5/0059
600/317
5,586,981 A 12/1996 Hu
(Continued)

FOREIGN PATENT DOCUMENTS

RU    2422081 C2    6/2011

*Primary Examiner* — Aaron F Roane

(57) ABSTRACT

The invention provides a non-invasive device comprising an optical system having a laser light source for generating a light beam, being configured such that, in use, the light beam exits the device and impinges on an outer surface of the skin to be treated; the optical system being configured to focus, in use, the light beam at a position of a treatment location inside the skin, whereby Laser Induced Optical Breakdown is induced at the position of the treatment location; an opening disposed such that, in use, light returning from the skin enters the device as a measurement light beam; and a first and second intensity detection channel configured and arranged to detect the intensity in, respectively, a first and a second bandwidth range of the measurement light beam, wherein the first and the second bandwidth ranges both comprise a wavelength of light produced in the skin as a result of Laser Induced Optical Breakdown, and the first bandwidth range comprises the Second Harmonic Generation wavelength of the laser light source, the second bandwidth range is adjacent to the first bandwidth range, and the second bandwidth range excludes the Second Harmonic Generation wavelength of the laser light source. The invention also provides a corresponding method to treat skin (30), in particular to reduce wrinkles. For the efficacy of such a treatment, two main parameters are crucial: the intensity at
(Continued)

the position of the treatment location and the focus depth, and it is also crucial that these parameters can be measured using the same measurement system.

8 Claims, 3 Drawing Sheets

(51) Int. Cl.
 *A61B 18/00* (2006.01)
 *A61B 17/00* (2006.01)
(58) Field of Classification Search
 CPC ........... A61B 2018/00702; A61B 2018/00738; A61B 2018/00785
 USPC ............................................................ 606/9
 See application file for complete search history.

(56) References Cited

U.S. PATENT DOCUMENTS

| | | | |
|---|---|---|---|
| 6,208,886 B1 | 3/2001 | Alfano | |
| 6,881,212 B1 | 4/2005 | Clement | |
| 2006/0004347 A1* | 1/2006 | Altshuler | A61B 18/203 606/4 |
| 2008/0015448 A1* | 1/2008 | Keely | A61B 5/0091 600/477 |
| 2008/0045865 A1 | 2/2008 | Kislev | |
| 2010/0063490 A1 | 3/2010 | Verhagen | |

\* cited by examiner

DEVICE FOR NON-INVASIVE TREATMENT OF SKIN USING LASER LIGHT

This application is the U.S. National Phase application under 35 U.S.C. § 371 of International Application No. PCT/I132014/059880, filed on Mar. 17, 2014, which claims the benefit of U.S. Provisional Application 61/804,254 filed Mar. 22, 2013. These applications are hereby incorporated by reference herein.

FIELD OF THE INVENTION

The invention relates generally to the treatment of skin using laser light, and more particularly to a non-invasive device and method comprising measurement steps to optimize the treatment parameters.

BACKGROUND OF THE INVENTION

The desire to maintain a youthful appearance by preventing or reducing wrinkles in the skin is an important issue in human society. Many techniques have been designed to address the above issue. One of the techniques, e.g., known from the published international patent application WO 2008/001284 A2, is to create a focal spot in a dermis layer of the skin to be treated. Said WO application discloses a skin treatment device with a laser source and focusing optics. The device emits a laser beam. The power of the laser is selected such that Laser Induced Optical Breakdown (LIOB) affects the skin in order to stimulate re-growth of skin tissue and reduces wrinkles. This LIOB is based on strong non-linear absorption of the laser light by the skin tissue, which occurs above a certain threshold value for the power density of the laser light. This strong absorption causes a very localized plasma that is able to damage or even remove tissue at the location of said plasma. This is caused by secondary, primarily mechanical, effects such as rapid expansion of the generated plasma. This effect is very local, because below the threshold, there is zero or very little linear and non-linear absorption, while above the threshold a plasma is generated, which absorbs the radiation even more strongly.

More details on LIOB may be found in the article "Minimally invasive non-thermal laser technology using laser-induced optical breakdown for skin rejuvenation", Habbema, Verhagen, van Hal, Liu and Varghese; J. Biophotonics 5, No. 2, 194-199 (2012); DOI 10.1002/jbio.201100083. As discussed in this article, LIOB occurs when the irradiance is sufficiently high to produce a critical free-electron density of about $10^{21}$ cm$^{-3}$.

An increasing number of these skin treatment devices are being provided for use by consumers instead of by medical professionals. These devices are non-invasive —they create an effect beneath the surface of the skin without having to physically penetrate the epidermis. However, such home use raises new concerns, such as safety and treatment efficacy. This is particularly important when the light source is a laser, and incorrect operation can result in scarring or burning of the skin where the laser light passes through the skin layers.

Damage to the epidermis, for example, is highly undesirable because this may lead to complications and health risks to the person being treated, as well as social downtime. If superficial lesions are created above the dermis, petechiae (micro-bleeding) may occur due to the micro-rupturing of capillaries, resulting in reduced efficacy and an increase in side effects. The formation of new collagen for the purpose of skin rejuvenation will occur if lesions are created in the collagen. At large focusing depths, the intensity in the focus may not reach the threshold required for optical breakdown and therefore the treatment may not produce the desired rejuvenation effects. The effectiveness of optical breakdown for skin rejuvenation depends on several factors such as optical and structural properties of the skin, laser light intensity in the focus, optical coupling etc. There is an upper limit for the photomechanical effect that can be used to induce growth of new collagen fibers for rejuvenation effects and treatment beyond this limit is not effective and additionally subjects the user to the dangers of over-use. Under-treatment is not preferred either because it may not produce the desired tightening effects.

SUMMARY OF THE INVENTION

An object of the invention is to provide a non-invasive skin treatment device and a method comprising measurement steps to optimize the treatment parameters.

The object is achieved according to the invention by a device comprising:
  an optical system having a laser light source for generating a light beam, being configured such that, in use, the light beam exits the device and impinges on an outer surface of the skin to be treated;
  the optical system being configured to focus, in use, the light beam at a position of a treatment location inside the skin, whereby Laser Induced Optical Breakdown is induced at the position of the treatment location;
  an opening disposed such that, in use, light returning from the skin enters the device as a measurement light beam; and
  a first and a second intensity detection channel configured and arranged to detect the intensity in, respectively, a first and a second bandwidth range of the measurement light beam, wherein the first and the second bandwidth ranges both comprise a wavelength of light produced in the skin as a result of Laser Induced Optical Breakdown, the first bandwidth range comprises the Second Harmonic Generation wavelength of the laser light source, the second bandwidth range is adjacent to the first bandwidth range and the second bandwidth range excludes the Second Harmonic Generation wavelength of the laser light source.

The object of the invention is also achieved by means of a method using a device generating laser light, the method comprising:
  providing an optical system having a laser light source for generating a light beam, being configured such that the light beam exits the device and impinges on an outer surface of the skin to be treated;
  focusing the light beam at a position of a treatment location inside the skin, whereby Laser Induced Optical Breakdown is induced at the position of the treatment location;
  disposing the device such that light returning from the skin enters the device through an opening as a measurement light beam;
  detecting the intensity in a first and a second bandwidth range of the measurement light beam, wherein the first and the second bandwidth ranges both comprise a wavelength of light produced in the skin as a result of Laser Induced Optical Breakdown (LIOB), wherein the first bandwidth range comprises the Second Harmonic Generation (SHG) wavelength of the laser light source, the second bandwidth range is adjacent to the first bandwidth range, and the second bandwidth range excludes the Second Harmonic Generation wavelength of the laser light source.

The intensity in the first bandwidth range is influenced by the intensity of light returning from the skin as a result of the occurrence of LIOB and the intensity of light returning as a result of SHG. The intensity in the second bandwidth range is mainly influenced by the intensity of light returning from the skin as a result of the occurrence of LIOB. The degree of SHG indicates the presence of collagen at the treatment depth. The degree of LIOB indicates that the laser light intensity in the focus is sufficient to generate optical breakdown. If no LIOB wavelength is detected, this may indicate that the laser light intensity should be increased. If no SHG wavelength of the laser light source is detected, this may indicate that the focus depth should be increased or decreased.

The invention is based on the insight that for the efficacy of such a treatment, two main parameters are crucial: the intensity at the position of the treatment location and the focus depth, and that these can be measured using the same measurement system. The optimal focus depth can be different, depending on the thickness of stratum corneum and epidermis, and this optimal depth varies for different individuals, and even varies for the same individual depending on where on the body the treatment is being performed.

It may be advantageous for the device to further comprise a processor connected to the first and the second intensity detection channel, the processor being configured to determine the occurrence of both Laser Induced Optical Breakdown and Second Harmonic Generation at the position of the treatment location based on the intensities detected by the first and the second intensity detection channel. Similarly, the method may further comprise processing the detected intensity in the first and the second bandwidth ranges to determine the occurrence of both Laser Induced Optical Breakdown and Second Harmonic Generation at the position of the treatment location, based on the detected intensities in the first and the second bandwidth ranges.

Processing the values of the intensities detected by the first and the second intensity detection channels may provide a more reliable and more accurate determination of the occurrence of LIOB and the presence of the SHG wavelength of the laser light source. The intensity in the second bandwidth range may indicate whether LIOB occurs, and the difference between the first and the second bandwidth range intensities may indicate whether the SHG wavelength of the laser light source is present. The intensity in the first bandwidth range depends both on whether LIOB occurs and whether the SHG wavelength of the laser light source is present.

It may also be advantageous for the processor of the device to be further configured to determine either an adjustment in the intensity of the laser light source, an adjustment in the position of the treatment location, or both, whereby Laser Induced Optical Breakdown and Second Harmonic Generation will occur. Similarly, the method may further comprise determining either an adjustment in the intensity of the laser light source, an adjustment in the position of the treatment location, or both, whereby Laser Induced Optical Breakdown and Second Harmonic Generation will occur.

Knowing whether LIOB and SHG are being produced is, in itself, valuable information about the treatment. However, if the treatment depth and intensity are not optimal, the user would like to know how to optimize the parameters of the device.

If the optical system of the device further comprises adjustable optical elements for focusing the light beam at the position of the treatment location, and the processor is further configured to adjust the position of the treatment location in accordance with the determined adjustment in position by adjusting the configuration of these adjustable optical elements, then an automatic focusing system may be provided to optimize the focus depth based upon the detected intensity of the SHG wavelength of the laser light source. If no SHG wavelength of the laser light source is detected, the position of the treatment location, or treatment depth, may be adjusted until the SHG wavelength of the laser light source is detected.

If the intensity of the laser light source is adjustable, and the processor is further configured to adjust the intensity of the laser light source in accordance with the determined adjustment in intensity, then an automatic intensity system may be provided to optimize the intensity at the position of the treatment location based upon the detected intensity of the LIOB wavelength. If no LIOB is detected, the intensity may be increased until LIOB is detected.

Providing a device comprising both SHG and LIOB detection, and adjustable optical elements and an adjustable laser light intensity, is particularly advantageous as the position of the treatment location and the intensity of the laser light source may be adjusted at the same time to efficiently achieve LIOB in the collagen.

It should be noted that items which have the same reference numbers in different Figures, have the same structural features and the same functions, or are the same signals. When the function and/or structure of such an item have been explained, there is no necessity for repeated explanation thereof in the detailed description.

DETAILED DESCRIPTION OF EXAMPLES

Figure 1:
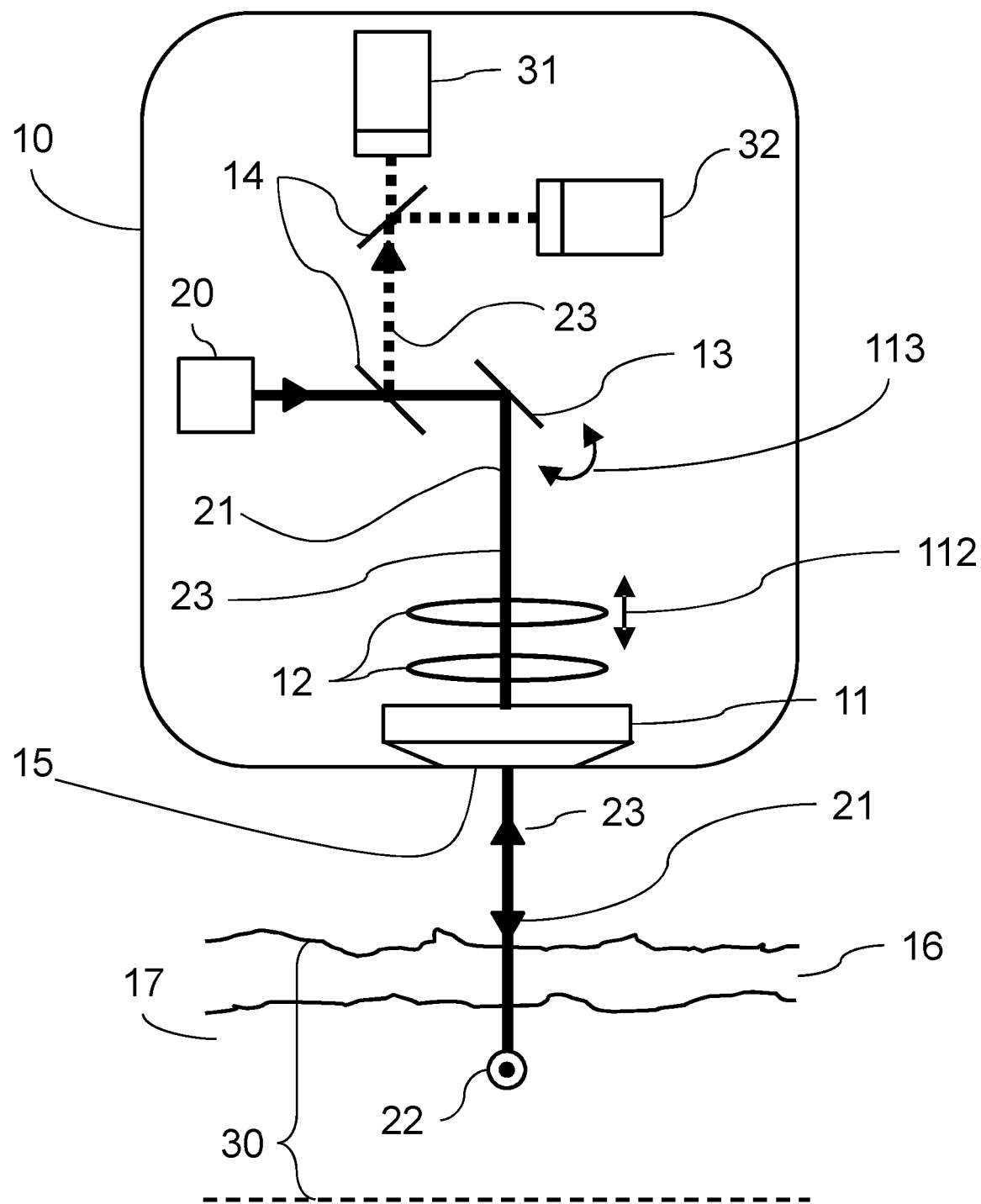
FIG. 1 diagrammatically shows the most important parts of the device when treating skin.

FIG. 1 schematically shows a skin 30 treatment device according to the invention, comprising an optical system 10. The optical system 10 comprises a laser light source 20 for providing an incident light beam 21 suitable for treating human or animal skin 30. The incident light beam 21 is typically generated using a pulsed laser—for example, Nd:YAG lasers with emission at 1064 nm and 1-1000 ps pulse duration.

Optical elements 12, 13 are provided in the optical system 10 for further modifying the light beam 21, and for focusing 22 the pulsed laser beam 21 inside the skin 30. Part or all of the optical elements may be provided in an interface element 11 which, during use of the device, is pressed onto or makes contact with the skin 30 to be treated. The light beam 21 exits the device through the interface element 11. Typically, an index-matching fluid is used to optically couple the incident light 21 into the skin 30.

The device is configured to create a focus 22 of the pulsed laser beam 21 at the position of the treatment location. If the device is being used to reduce wrinkles in the skin 30, the target location is in the collagen of the dermis 17 in order to create microscopic lesions at the position of the treatment location, which results in new collagen formation.

The invention uses the circumstance that the skin transmits electromagnetic radiation that is to be focused in the dermis, in a very small focal spot. To maximize this effect, a wavelength of the light is between 800 and 1100 nm. In this range, transmission is high and scattering and linear absorption are low. Thus, LIOB may be achieved easily, accurately (i.e. very locally) and efficiently. It is however not excluded to use other wavelengths.

In particular, the predetermined pulse time is between 100 ps and 10 ns. In this range, the plasma generated by the LIOB is very local, i.e. has a small spatial extension, which minimizes the risk of unintended damage to surrounding tissues. Furthermore, the peak power required to obtain LIOB is substantially independent of the pulse time in this range. However, other pulse times, e.g. in the range of about 100 fs to 100 ps, may also be used, and even pulse times in the ns and ms ranges.

Typically, the deliverable energy level in the laser beam pulse is between 0.1 and 10 mJ, measured at the surface of the skin. Such energy levels have turned out to be useful in the treatment, i.e. creating sufficient damage to stimulate new tissue growth. More specifically, the energy level is between about 0.5 and 5 mJ, and typically about 1 mJ. However, other energy levels are not excluded, such as levels up to about 20 mJ for large treatment depths up to 2 mm. In the above energy level indications, the energy is measured at the surface of the skin, i.e. it relates to the energy actually emitted into the skin.

Preferably, the deliverable energy level in the laser beam pulse is between 0.1 and 5 mJ, measured in a plasma generated by the LIOB phenomenon. More preferably, said energy level is between about 0.5 and 5 mJ, typically about 1 mJ. These energy levels are measured, or estimated, to be actually involved in the plasma of the LIOB phenomenon. Optical breakdown inside the skin and the resulting skin rejuvenation effects occur when the intensity of photons in the focus of an ultra-short near-infrared laser pulse exceed the threshold ($\sim 10^{12}$ W/cm2) required for optical breakdown. In all of the above, it is to be understood that instead of a single pulse, it is also possible to provide a number of pulses, as long as the pulses generate a LIOB phenomenon.

The optical elements found in the optical system 10 may comprise one or more lenses 12 for converging and/or diverging the light beam 21, and one or more mirrors 13 for deflecting the light beam in a desired direction. The exact position and/or orientation of the optical elements may be adjustable using techniques known in the art 112, 113, to adapt the position and quality of the focus 22 as required for generating LIOB at the desired position of the treatment location. Focus control may be provided by adjusting the position of 112 one or more of the lenses 12 and/or rotating one or more of the mirrors 13.

The number and positions of lenses 12 and mirrors 13 are determined by the disposition of the components within the optical system 10 and the desired degrees of adjustment that the skilled person wishes to provide. For example, the adjustable lenses 12, 112 may comprise a lens with a distance setting, or may be a zoom lens. The adjustable mirror 13, 113 may comprise a mirror that is rotatable in one or more, preferably two, directions. The mirror may be flat, e.g. when combined with a lens, or may be concave, in particular if the mirror provides focusing action. Advantageously, the adjustable lens 12, 112 may comprise an autofocus lens. Such a lens is automatically adjusted with respect to the skin surface. This ensures a correct treatment depth in almost all circumstances. In another example, the optical system 10 may further comprise a laser beam manipulator for positioning the focal spot 22. Such a laser beam manipulator may comprise, for example, a moveable mirror and a mirror actuator for adjusting the position of the mirror, as well as a control unit. The laser beam manipulator may also comprise the adjustable lens or mirror. The laser beam manipulator may be used for positioning the focal spot on and in the skin 30. The user may control the laser beam manipulator.

The device further comprises a measurement opening 15, which is disposed such that light returning from the skin enters the device as a measurement light beam 23. In the preferred embodiment depicted in FIG. 1, in use, the measurement light beam 23 returns along substantially the same path as the exiting light beam 21 as provided by a compact device. At an appropriate position on a path of the measurement light beam 23, the optical system 10 is further provided with one or more optical elements 14, configured and arranged to direct the measurement light beam 23 towards the measurement system. In the example of FIG. 1, a beam splitter 14 is used to separate a path of the returning measurement light beam 23 from a path of the laser light beam 21 at an appropriate position.

The optical system 10 further comprises appropriate optical elements, arranged and configured to provide two intensity detection channels. The first channel is configured to detect the intensity over a bandwidth range which comprises the SHG wavelength of the laser light source. For example, for a laser source 20 with a wavelength of 1064 nm, the first bandwidth range may be 532 nm±10 nm. The second channel is configured to detect the intensity over a bandwidth range adjacent to the first bandwidth range, which does not comprise the SHG wavelength of the laser light source, but which does comprise a wavelength produced when LIOB occurs in the skin. For example, for a laser source 20 with a wavelength of 1064 nm, the second bandwidth range may be 544 m±10 nm or 520±10 nm. As depicted in FIG. 1, the channels may be arranged and configured by providing a photodetector 31,32 with an appropriate bandpass filter, such as a bandpass interference filter, and providing a splitting optical component on the measurement light beam 23 path to direct a portion of the measurement light beam to each detector. This splitting optical component may also be configured to select the wavelength bandwidth range in each portion, for example, by using a harmonic separator mirror or a dichroic beam splitter. The skilled person will be able to devise many different combinations of mirrors, splitters and filters that will achieve the same purpose, namely to measure the intensity over two adjacent bandwidth ranges.

The skin 30 comprises multiple layers with different optical properties. The epidermis 16 is composed of the outermost layers and forms a waterproof protective barrier. The outermost layer of the epidermis is the stratum corneum which, due to its microscopic fluctuations in roughness, impedes the coupling of light between the device 10 and the skin 30. Underneath the epidermis 16, the dermis 17 is situated. The dermis 17 comprises the collagen fibers at which the skin treatment is aimed.

The device, and in particular the optical system 10, are configured to produce LIOB at the focus 22 by selecting or modifying one or more optical properties of the exiting light beam 21. The convergence of the light beam 21 into a focal spot 22 helps localize the LIOB phenomenon and helps prevent damage to the epidermis 16, because there the power density is much lower than in the focal spot 22 in the dermis 17. A device for determining the orientation of collagen by detecting the SHG light is known from Japanese patent application 2008-081503, publication number 2009-236610, published 15 Oct. 2009, by applicant Osaka Univ and Shiseide Co Ltd.

SHG wavelengths are generated in nonlinear optical processes in which photons interacting with collagen, a nonlinear material, are effectively combined to form new photons with twice the energy, and therefore twice the frequency and half the wavelength of the initial photons. In addition to second harmonics, also third and higher harmonics are generated. All references to SHG should be understood to encompass also third and higher harmonics because these may also be used.

Typically, collagen is found approximately at a depth of approximately 0.35 mm. This is based on a typical total thickness of the epidermis 16 with the stratum corneum, in the face, of between 0.06 and 0.2 mm and a typical thickness of the dermis layer of 2 mm. In particular cases, the epidermis 16 and/or dermis 17 may be thinner or thicker, or may be present at a slightly different depth, such as on other parts of the body, e.g. the hands.

To determine possible values for the first and the second bandwidth ranges, measurements were performed, using a pulse laser source 20 with a wavelength of 1064 nm focused into skin. The light returning from the skin was analysed using a spectrophotometer, and these results are depicted in FIGS. 2A and 2B.

Figure 2A:
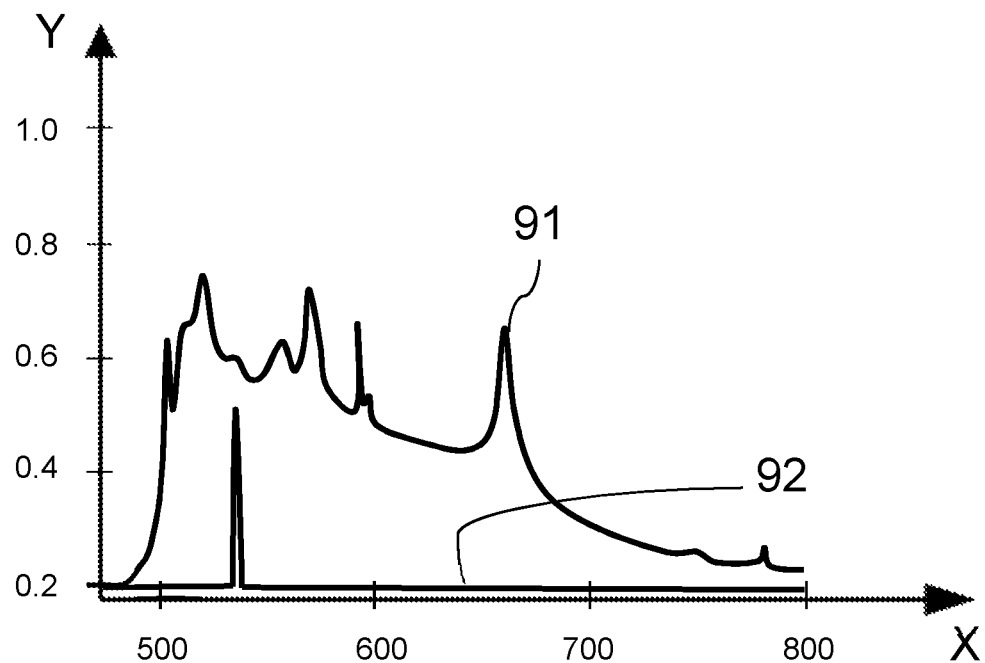
FIG. 2A shows an example of the intensity spectrum recorded using a spectrophotometer, wherein SHG is detected without LIOB and LIOB is detected without SHG.
Figure 2B:
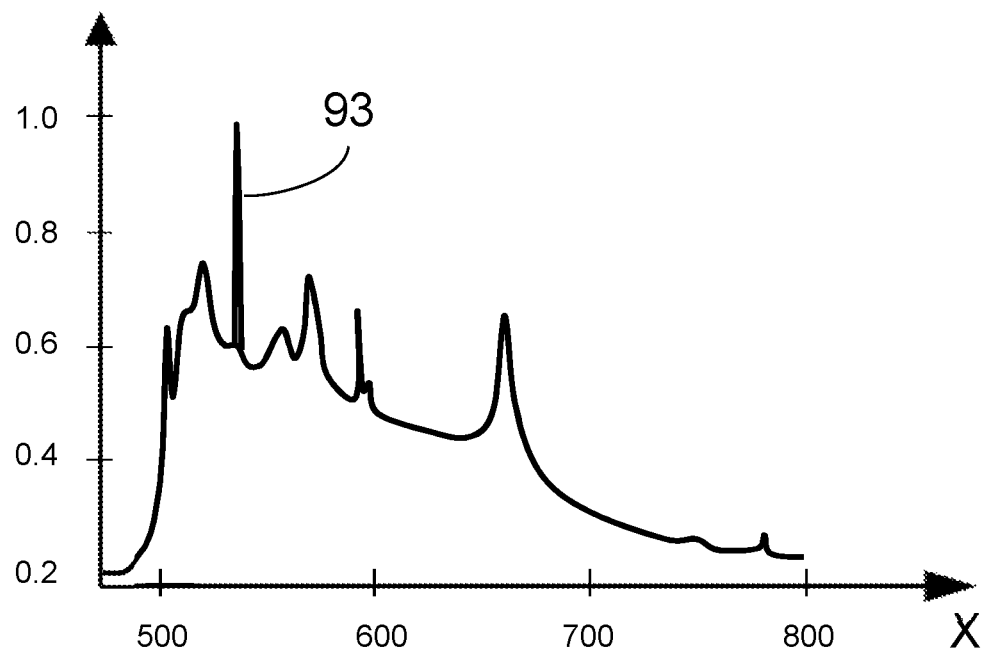
FIG. 2B shows an example of the intensity spectrum recorded using a spectrophotometer, wherein SHG is detected with LIOB.

FIG. 2A shows the relationship between intensity when LIOB is generated without SHG 91 and intensity when SHG is generated without LIOB 92. The horizontal axis (X) represents a continuous spectrum of the wavelength in nm from 470 to 800—the axis is marked in steps of 100 nm. The vertical axis (Y) represents the normalized intensity measured at each point in the spectrum, from 0.2 to 1.0. The measurements were normalized such that the maximum intensity measured at the peak of the SHG wavelength of the laser light source as a result of LIOB (depicted in FIG. 2B) represents 1.0.

The spectrum of LIOB generated without SHG 91 was produced by focusing at a depth in the skin where no collagen was present. Using approximate values, the basic level of the spectrum rises from 0.2 at 480 nm to 0.6 at 525 nm, and then slowly decreases to 0.25 at 750 nm. Peaks rising above this basic level are at 0.64/500 nm, 0.75/516 nm, 0.65/553 nm, 0.72/567 nm and 0.66/590 nm. From the basic level, a valley is also depicted at 0.57/540 nm.

The spectrum of SHG generated without LIOB 92 was produced by focusing in collagen with a laser light intensity insufficient to generate LIOB. The basic level of this spectrum is a flat line at 0.2 from 475 nm to 800 nm, with a single peak of 0.5 at 532 nm. The peak is about 4 nm wide at the point where it leaves the basic level.

FIG. 2B shows the spectrum 93 generated when LIOB is generated in collagen that is, the laser light intensity was sufficient to generate LIOB and the focus 22 was selected to be in collagen where the SHG was generated. The spectrum 93 depicted is the same as that when the "LIOB is generated without SHG 91" as shown in FIG. 2A, combined with the SHG peak at 532 nm, where the SHG+LIOB peak reaches 1.0 for the normalized intensity and has a width of approximately 4 nm where the SHG peak leaves the LIOB intensity spectrum.

Figure 3:
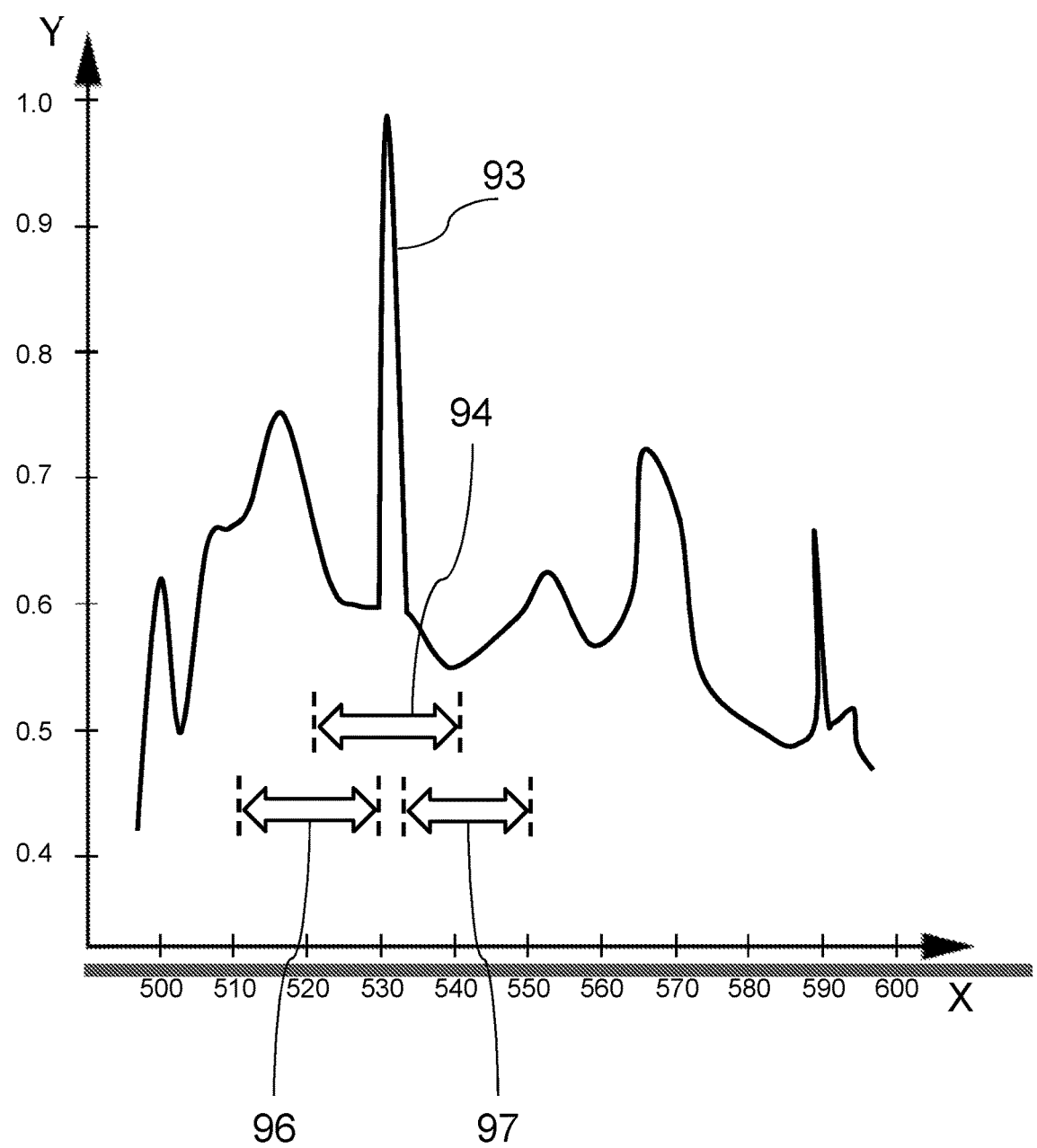
FIG. 3 depicts, schematically, an enlarged portion of the spectrum of FIG. 2B, wherein possible bandwidth ranges for the intensity detection channels are indicated.

FIG. 3 depicts, schematically, an enlarged portion of the spectrum 93 of FIG. 2B where possible bandwidth ranges for the intensity detection channels are indicated. A section of the spectrum from 500 nm to 600 nm has been enlarged schematically to illustrate how the bandwidth ranges may be selected. A first bandwidth range of 532 nm±10 nm 94 is depicted by an arrow, together with two possibilities for the second bandwidth range—544 m ±10 nm 97 or 520±10 nm 96, which are also depicted by arrows.

For the example device of FIG. 1, where intensity is to be measured over two bandwidth ranges, the first bandwidth range should comprise the SHG wavelength of the laser light source to enable detection of the peak. As this wavelength is half the laser source 20 wavelength, this value is determined by the laser source used. The top and bottom end of the first bandwidth range should be selected to ensure that variation in the SHG wavelength of the laser light source does not affect the detection. These fluctuations may be determined by performing a suitable number of measurements on different individuals and different areas of skin. In the preferred embodiment, a range of ±10 nm around 532 nm is selected because bandwidth filters in this range are easily available.

The second bandwidth range 96, 97 is selected such that the intensity detected in this bandwidth range is unaffected by the SHG wavelength of the laser light source, but the intensity detected when LIOB occurs without SHG, that is LIOB not in collagen, should be approximately the same in the first wavelength range 94 as in the second wavelength range 96, 97. This is what is meant by the term "adjacent to", and this includes the situation where the first and second bandwidth ranges overlap, and the situation where there is no overlap. In the example depicted, the second wavelength range has been selected so that it excludes the SHG peak, which was approximately 532 nm±2 nm, resulting in 544 m±10 nm 97 or 520±10 nm 96 as possibilities. In practice, it may be sufficient to just exclude the SHG wavelengths which correspond to the top of the SHG peak, such as 532 nm±0.5 nm, 532 nm±1 nm or 532±1.5 nm. The range to be excluded therefore depends on the effect of the SHG peak on the intensity detected in the second bandwidth range. In practice, it will mainly depend on the fluctuations to be expected in the peak wavelength distribution and the size of the peak. In all cases, the second bandwidth range will exclude at least the SHG wavelength of the laser light source of 532 nm.

The use of the term "average" should be understood to represent any suitable measure of central tendency in the intensity values, such as mean, median, mode. The determination used depends upon the detection method, the intensity data available and the arithmetic processing facilities provided in the device.

When determining the degree of similarity between the intensity detected in the first 94 and second wavelength 96, 97 ranges, that is when LIOB occurs but not in collagen, background fluctuations in intensity should be taken into account. Fluctuations seen in the LIOB-only spectrum 91 are no more than approximately 0.15—this is less than half of the difference between no LIOB and LIOB, which is approximately 0.4 in the region 510 to 550 nm. It is also less than half of the difference between no SHG and SHG, which is approximately 0.4 at 532 nm.

As the skilled person will appreciate, these measurement results confirm that it is possible to define two adjacent bandwidth ranges that allow the invention to be implemented. Using the example given with a first bandwidth range 94 of 532 nm±10 nm and a second bandwidth range 97 of 544 m±10 nm 97, a significant difference in average intensity in the first bandwidth range 94 of 0.3 or more indicates SHG generation, and an increase in the average of both first 94 and second 97 bandwidth ranges of 0.4 or more indicates LIOB generation.

The skilled person will be able to select the two adjacent bandwidth ranges enabling to achieve the LIOB and collagen detection by routine measurements and simulations. The first and second bandwidth ranges may be of the same or differing width—selection is determined by the accuracy and reliability of the LIOB and SHG detection achieved in the bandwidth ranges. Some examples of suitable bandwidth ranges, including some of the examples just given, are:

| $1^{st}$ bandwidth range 94 for SHG | $2^{nd}$ bandwidth range 96, 97 for LIOB |
|---|---|
| 532 nm ± 10 nm (522-542 nm) | 544 nm ± 10 nm (534-554 nm) |
| 532 nm ± 10 nm (522-542 nm) | 520 nm ± 10 nm (510-530 nm) |
| 532 nm ± 10 nm (522-542 nm) | 554 nm ± 10 nm (544-564 nm) |
| 532 nm ± 10 nm (522-542 nm) | 510 nm ± 10 nm (500-520 nm) |
| 532 nm ± 2 nm (530-534 nm) | 546 nm ± 10 nm (536-556 nm) |
| 532 nm ± 2 nm (530-534 nm) | 518 nm ± 10 nm (508-528 nm) |
| 532 nm ± 2 nm (530-534 nm) | 544 nm ± 10 nm (534-554 nm) |
| 532 nm ± 2 nm (530-534 nm) | 524 nm ± 10 nm (514-534 nm) |
| 532 nm ± 2 nm (530-534 nm) | 538 nm ± 2 nm (536-540 nm) |
| 532 nm ± 2 nm (530-534 nm) | 526 nm ± 2 nm (524-528 nm) |
| 532 nm ± 2 nm (530-534 nm) | 543 nm ± 10 nm (533-553 nm) |
| 532 nm ± 2 nm (530-534 nm) | 521 nm ± 10 nm (511-531 nm) |
| 532 nm ± 2 nm (530-534 nm) | 536 nm ± 2 nm (534-538 nm) |
| 532 nm ± 2 nm (530-534 nm) | 528 nm ± 2 nm (526-530 nm) |

In the simplest embodiment, the two intensity detection channels may be connected to electronic threshold detection, using conventional techniques, such that the operator is given a first warning if LIOB does not occur and a second warning if no SHG wavelength of the laser light source is detected.

It will be obvious to the skilled person that more than two intensity detection channels may also be used. This may be advantageous in optimizing the reliability of LIOB and SHG detection. An example thereof is a first bandwidth range of 532 m±10 nm 94 and a second bandwidth range comprised of two sub-ranges adjacent to the first bandwidth range, for example 544 m±10 nm and 520±10 nm. In that case, the average intensity in the second bandwidth range is determined by the average intensity in the sub-ranges.

It may be advantageous for the device to comprise a processor to determine whether LIOB occurs and whether SHG is generated at the position of the treatment location, based on the intensities detected by the first and second intensity detection channel. In the simplest embodiment, the average intensity in the first bandwidth range is compared to the average intensity in the second. A processor may allow a more flexible and reliable detection because other parameters, such as proximity of the device to the upper layer of the skin, may be incorporated, or values measured may be averaged over several measurements, or values may be compared to expected values in lookup tables.

It may also be advantageous for the device to comprise a processor to determine an adjustment in laser light intensity and/or an adjustment in focus which should be performed to generate LIOB and SHG. The difference between the intensity channels is a measure of focus adjustment, and the average intensity of both channels is a measure of adjustment in laser light intensity. This may be determined from the intensity detection channels by comparing the levels with stored reference values to do the calculation. If the optical system comprises adjustable optical elements and a laser light source having an adjustable laser light intensity, the processor may also be employed to make fine optimization scans during use to ensure that the LIOB and SHG intensities are maximized. The processor may also be employed to scan through different focus levels at a lower laser light intensity to determine the approximate depth where the collagen is located by detecting the SHG signal.

It is usually quicker and more convenient to simulate some or all of these measurements, for example using Matlab and adjusting the parameters to be as close as possible to the measurement conditions depicted in FIGS. 2A and 2B.

The invention provides a means of creating deep lesions inside dermis, using LIOB within collagen. Such a device and method may be used for the treatment of wrinkles and fine lines.

The laser light source 20 may be disposed outside of the optical system 20, and connected to the optical system 20 using an optical fiber. This provides a small, lightweight applicator unit, with the bulkier and heavier laser source etc., in a separate and stationary unit.

In the embodiment of FIG. 1, the light beam 21 exiting the device passes through the interface element 11, and the measurement light beam 23 enters the device through an opening 15 which is also disposed in the interface element 11. However, the opening 15 may be separate from the interface element 11, providing a completely separate path for the measurement light beam 23 compared to the light path 21.

Alternatively, the detectors 31, 32 may be integrated into the interface element 11, simplifying the optical design of the device.

The two detectors 31, 32 of FIG. 1 may be replaced with a single photodetector provided with a variable bandwidth filter, or a mechanical exchanger to switch between bandwidth filters.

The measurement system may also comprise a spectrophotometer, allowing the wavelength spectrum to be captured, and a processor to analyse the results in detail. Such a use of a processor also allows the bandwidth ranges and SHG/LIOB detection algorithms to be adapted due to, for example, changes in the optical properties of the skin, use of the device by different individuals or use of the device on a different area of the body.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:
1. A non-invasive device for treatment of skin using laser light, the device comprising:
   an optical system having a laser light source for generating a light beam, being configured such that, in use, the light beam exits the device and impinges on an outer surface of the skin to be treated;

the optical system being configured to focus, in use, the light beam at a position of a treatment location inside the skin, whereby Laser Induced Optical Breakdown is inducible at the position of the treatment location;

an opening disposed such that, in use, light returning from the skin enters the device as a measurement light beam; and a first and a second intensity detection channel configured and arranged to detect the intensity in, respectively, a first and a second bandwidth range of the measurement light beam, wherein:

the first and the second bandwidth ranges both include a wavelength of the measurement light beam producible in the skin as a result of Laser Induced Optical Breakdown at the position of the treatment location, the first bandwidth range further includes a Second Harmonic Generation wavelength of the measurement light beam producible in the skin as a result of a Second Harmonic Generation at the position of the treatment location, the second bandwidth range is adjacent to the first bandwidth range, and the second bandwidth range excludes the Second Harmonic Generation wavelength of the measurement light beam producible in the skin as a result of a Second Harmonic Generation at the position of the treatment location.

2. A device according to claim 1, wherein the device further comprises a processor connected to the first and the second intensity detection channel, the processor being configured to determine the occurrence of both Laser Induced Optical Breakdown and Second Harmonic Generation at the position of the treatment location, based on the intensities detected by the first and the second intensity detection channels.

3. A device according to claim 2, wherein the processor is further configured to determine either an adjustment in the intensity of the laser light source, an adjustment in the position of the treatment location, or both, whereby Laser Induced Optical Breakdown and Second Harmonic Generation will occur.

4. A device according to claim 3, wherein the optical system further includes adjustable optical elements for focusing the light beam at the position of the treatment location inside the skin, and wherein the processor is further configured to adjust the position of the treatment location by adjusting the configuration of the adjustable optical elements.

5. A device according to claim 3, wherein the intensity of the laser light source is adjustable, and wherein the processor is further configured to adjust the intensity of the laser light source.

6. A device according to claim 1, wherein the position of the treatment location is in a dermis layer of the skin to be treated.

7. A device according to claim 1, wherein the position of the treatment location is between 0.2 and 2 mm below the outer surface of the skin.

8. A device according to claim 1, wherein the first and the second intensity detection channel each include an optical bandpass filter and a photodetector in a path of the measurement light beam, wherein the bandpass filter is configured to allow respectively the first and the second bandwidth range of wavelengths to pass through to the photo detector.

* * * * *